US010403398B2

(12) United States Patent
Pidathala et al.

(10) Patent No.: US 10,403,398 B2
(45) Date of Patent: Sep. 3, 2019

(54) EFFICIENT MANAGEMENT OF VISIBLE LIGHT STILL IMAGES AND/OR VIDEO (71) Applicant: KONINKLIJKE PHILIPS N.V., Eindhoven (NL)

(72) Inventors: Uma Pidathala, Foster City, CA (US); Roshan Davis, San Mateo, CA (US); Swapnil Vinod, Sunnyvale, CA (US); Sitaram Baldwa, Foster City, CA (US)

(73) Assignee: Koninklijke Philips N.V., Eindhoven (NL)

( * ) Notice: Subject to any disclaimer, the term of this patent is extended or adjusted under 35 U.S.C. 154(b) by 97 days.

(21) Appl. No.: 15/528,128

(22) PCT Filed: Nov. 19, 2015

(86) PCT No.: PCT/IB2015/058960
§ 371 (c)(1),
(2) Date: May 19, 2017

(87) PCT Pub. No.: WO2016/083955
PCT Pub. Date: Jun. 2, 2016

(65) Prior Publication Data
US 2017/0323053 A1 Nov. 9, 2017

Related U.S. Application Data (60) Provisional application No. 62/084,591, filed on Nov. 26, 2014.

(51) Int. Cl.
*A61B 5/00* (2006.01)
*G16H 30/20* (2018.01)
(Continued)

(52) U.S. Cl.
CPC ........... *G16H 30/20* (2018.01); *G06F 3/0482* (2013.01); *G06F 3/04842* (2013.01);
(Continued)

(58) Field of Classification Search
CPC .............. G06F 3/00; H04N 5/00; G06T 11/00
(Continued)

(56) References Cited

U.S. PATENT DOCUMENTS 5,058,148 A * 10/1991 Plut ........................ H04N 5/32
348/E5.086
8,700,432 B2    4/2014 Letts
(Continued)

OTHER PUBLICATIONS

"IBM Research Unveils 3D Avatar to Help Doctors Visualize Patient Records and Improve Care", https://www-03.ibm.com/press/us/en/pressrelease/22375.wss.

*Primary Examiner* — Abolfazl Tabatabai (57) ABSTRACT

A visible light imaging system includes acquisition circuitry, an image generator that generates at least one of a visible light image and a visible light video with light sensed by the acquisition circuitry, a memory, and a controller. The controller, in response to executing instructions of the memory: launches a scan application, visually presents a first soft tool that retrieves an identification of a subject of interest to an imaging study based on a user input, obtains at least one of a visible light image and a visible light video, which is generated by the acquisition circuitry and the image generator for the subject, associates the retrieved identification of the subject and the at least one of the image and the video, and transfers the at least one of the image and the video, the identification of the subject, and the association to a data repository.

15 Claims, 7 Drawing Sheets

(51) Int. Cl.
| | |
|---|---|
| *G06F 19/00* | (2018.01) |
| *H04N 5/272* | (2006.01) |
| *H04N 5/232* | (2006.01) |
| *H04N 5/225* | (2006.01) |
| *G06F 3/0482* | (2013.01) |
| *G06F 3/0484* | (2013.01) |
| *G06T 11/60* | (2006.01) |
| *A61B 5/02* | (2006.01) |

(52) U.S. Cl.
CPC ............ *G06F 19/00* (2013.01); *G06F 19/321* (2013.01); *G06T 11/60* (2013.01); *H04N 5/2252* (2013.01); *H04N 5/23216* (2013.01); *H04N 5/272* (2013.01); *G06T 2200/28* (2013.01); *G06T 2210/41* (2013.01)

(58) Field of Classification Search
USPC .................................. 382/128–134; 600/300
See application file for complete search history.

(56) References Cited

U.S. PATENT DOCUMENTS

| | | | |
|---|---|---|---|
| 9,595,115 B1* | 3/2017 | Cederlof | ................... G06T 7/20 |
| 2012/0120220 A1 | 5/2012 | Al-Moosawi | |
| 2013/0174077 A1 | 7/2013 | Asami et al. | |
| 2014/0126770 A1 | 5/2014 | Odessky et al. | |
| 2014/0180717 A1 | 6/2014 | Mihara | |
| 2014/0193056 A1 | 7/2014 | Neff | |
| 2016/0354155 A1 | 12/2016 | Hodges et al. | |

* cited by examiner

EFFICIENT MANAGEMENT OF VISIBLE LIGHT STILL IMAGES AND/OR VIDEO

CROSS-REFERENCE TO PRIOR APPLICATIONS

This application is the U.S. National Phase application under 35 U.S.C. § 371 of International Application No. PCT/IB2015/058960, filed on Nov. 19, 2015, which claims the benefit of U.S. Provisional Application No. 62/084,591, filed on Nov. 26, 2014. This application is hereby incorporated by reference herein.

FIELD OF THE INVENTION

The following generally relates to visible light still images and/or video and more particularly to efficient management of visible light still images and/or video.

BACKGROUND OF THE INVENTION

A visible light still image (e.g., a photograph) is an image produced with acquired data having a wavelength in a range of four hundred to seven hundred nanometers (400-700 nm) in the electromagnetic spectrum. Electromagnetic radiation in this range is visible to the human eye and is referred to as visible light, in contrast to other ranges of the electromagnetic spectrum, which include electromagnetic radiation that is visible to the human eye.

An example device that is configured to sense visible light used to produce a visible light image and/or video includes a sensor that is sensitive to visible light and corresponding processing circuitry. Examples of such devices include, but are not limited to, a smartphone, smartglasses, a tablet, a laptop, an endoscope, a microscope, a colposcope, a retinoscope, a digital camera, and a digital video recorder.

In the clinical setting, the visible light images, for example, are stored locally on the visible light imaging system and/or on a computing device (e.g., a computer console). Unfortunately, with such storage, there is a risk of possible patient privacy violations and/or delays in diagnosis. As such, there is an unresolved need for efficient management of visible light images and/or visible light video.

SUMMARY OF THE INVENTION

Aspects described herein address the above-referenced problems and others.

In one aspect, a visible light imaging system includes acquisition circuitry configured to sense visible light and generate a signal indicative thereof, an image generator configured to generate at least one of a visible light image and a visible light video with the signal; a memory configured to store a scan module, which includes computer executable instructions, and a controller. The controller, which, in response to executing the computer executable instructions: launches a scan application of the visible light imaging system, visually presents, in response to a first input signal, a first soft tool that retrieves an identification of a subject of interest to an imaging study based on a user input, obtains at least one of a visible light image and a visible light video of the subject of interest, associates the retrieved identification of the subject and the at least one of the visible light image and the visible light video of the subject, and transfers the at least one of the visible light image and the visible light video, the identification of the subject, and the association to a data repository (106).

In another aspect, a method includes launching a scan application of a single enclosure, hand-hand visible light imaging system, identifying a subject to image with the scan application by a subject identification from pre-stored identifications stored in memory of the single enclosure, hand-hand visible light imaging system using an input device of the single enclosure, hand-hand visible light imaging system, capturing at least one of an image and a video of a body part with acquisition circuitry and an image generator of the single enclosure, hand-hand visible light imaging system, transferring, with a controller and through a physical communication interface, the at least one of the image and the video along with the subject identification to a data repository, and removing the at least one of the image and the video from the single enclosure, hand-hand visible light imaging system.

In another aspect, a method includes capturing at least one of an image or video of a body part with acquisition circuitry and an image generator of a visible light imager of a visible light imaging system, launching a scan application of a visible light console of the visible light imaging system, identifying a subject to image with the scan application by a subject identification from pre-stored identifications stored in memory of the visible light console using an input device of the visible light console, uploading the captured at least one of image or video of the body part from the visible light imager to the visible light console, transferring, with a controller and through a physical communication interface, the uploaded at least one of image and video along with the subject identification to a data repository, and removing the at least one of image and video from the visible light console.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
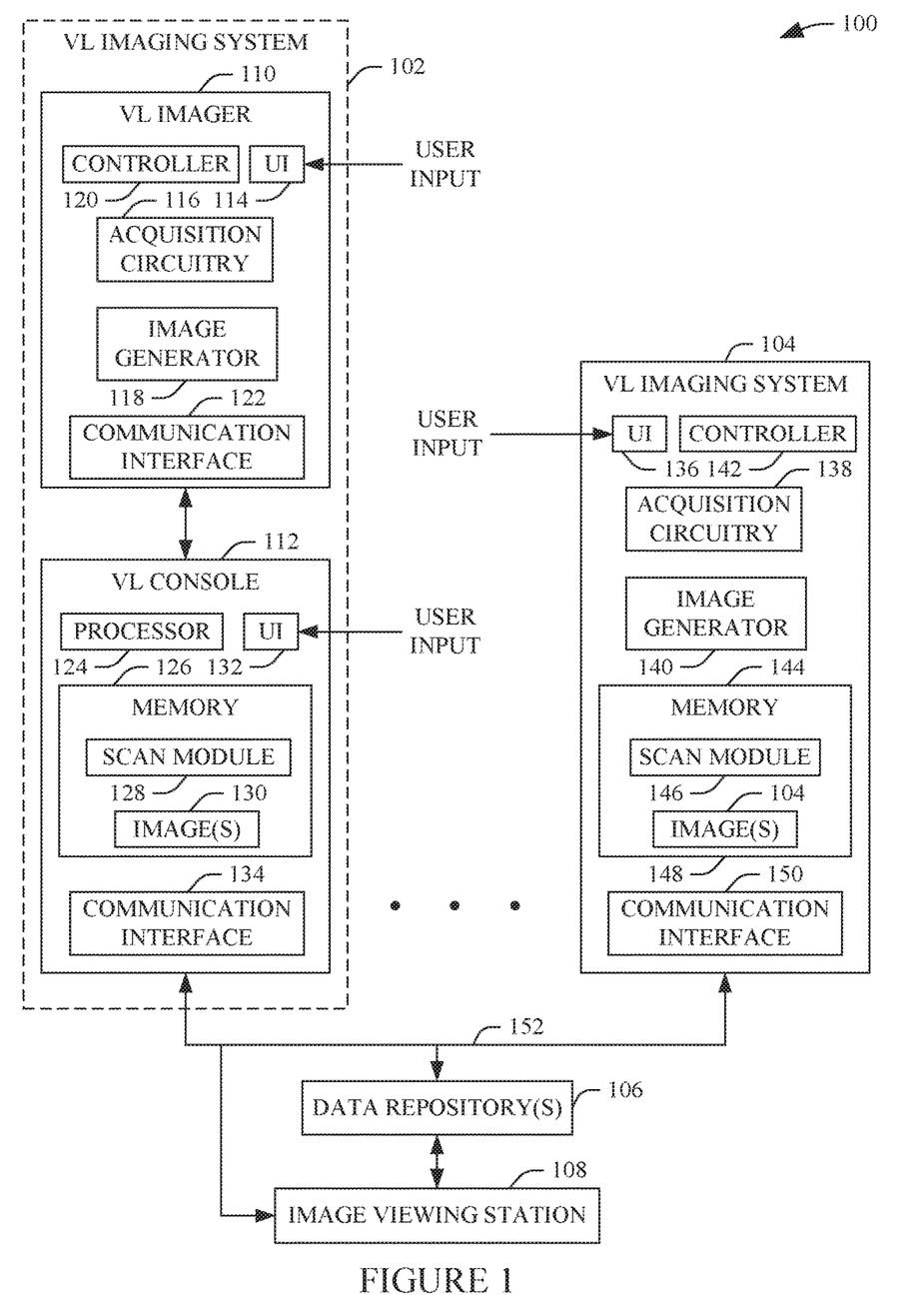
FIG. 1 schematically illustrates an example system including one or more visible light imaging systems.

FIG. 1 schematically illustrates a system 100 with N of visible light (VL) imaging systems 102, . . . , 104 (where N is a positive integer), a data repository 106 and at least one an image viewing station 108.

The visible light imaging system 102 includes a VL imager 110 and a VL console 112. In the illustrated embodiment, the VL imager 110 and the VL console 112 are separate devices that are electrically interfaced through complementary wireless communication circuitry and/or a hardwired channel between complementary physical communication connectors. For example, in one instance, the VL imager 110 includes an endoscope or glasses, and the VL console 112 includes a computer, which are electrically interfaced through a cable.

In the illustrated example, the VL imager 110 includes a user interface (UI) 114, an acquisition circuitry 116, an image generation engine 118, a controller 120, and a communication interface 122. The UI 114, in one instance, includes one or more input devices such as a physical button, a knob, a switch, etc. The UI 114 also includes an output device such as a visual indicator (e.g., LED, seven segment display, etc.), a speaker, etc. The acquisition circuitry 116 includes a sensor that senses or detects visible light. The image generation engine 118 is configured to generate a VL image from the sensed visible light.

The controller 120 controls at least the acquisition circuitry 116 and the image generation engine 118. The controller 120, in response to receiving, e.g., from the UI 114, a signal indicative of actuation of a start imaging control of the UI 114, activates the acquisition circuitry 116 to sense visible light and the image generation engine 118 to generate an image from the sensed visible light. The communication interface 122 includes a wireless electrical interface and/or an electro-mechanical physical connector.

The VL console 112 includes a processor 124 (e.g., a microprocessor, a central processing unit, etc.), a memory 126 which stores application software, such as a scan module 128 with computer executable instructions, and data, which includes images 130 (in the illustrated example), a user interface (UI) 132, and a communication interface 134. The UI 132, in one instance, includes one or more input devices such as a touch screen, a physical button, a knob, etc. The UI 132 also includes an output device such as a display screen, a visual indicator (e.g., LED, seven segment display, etc.), a speaker, etc.

The processor 124, in response to executing one or more of the computer executable instructions of the scan module 128, runs a scan application. As described in greater detail below, in one instance, running the application causes visual presentation of a graphical user interface (GUI) with software tools for linking a subject identification and/or an imaged body part identification to a VL image and/or VL video acquired by the VL imaging system 102. The communication interface 134 includes a wireless electrical interface and/or an electro-mechanical physical connector.

The visible light imaging systems 104 includes a user interface (UI) 136, an acquisition circuitry 138, an image generation engine 140, a controller (or controller) 142 a memory 144 which stores application software, such as a scan module 146 with computer executable instructions, and data, which includes images 148 (in the illustrated example), and a communication interface 150. The UI 136, in one instance, includes one or more input devices such as a touch screen, a physical button, a knob, etc. The UI 136 also includes an output device such as a display screen, a visual indicator (e.g., LED, seven segment display, etc.), a speaker, etc.

The acquisition circuitry 138 includes a sensor that senses or detects visible light. The image generation engine 140 is configured to generate an image from the sensed visible light. The controller 142 controls at least the acquisition circuitry 138 and the image generation engine 140. The controller 142, in response to receiving, from the UI 136, a signal indicative of actuation of a start imaging control of the UI 136, activates the acquisition circuitry 138 to sense visible light and the image generation engine 140 to generate an image from the sensed visible light.

The controller 142, in response to executing one or more of the computer executable instructions of the scan module 146, runs a scan application. As described in greater detail below, in one instance, running the imaging editor application causes visual presentation of a graphical user interface (GUI) with software tools for including linking a subject identification and/or an imaged body part identification to a VL image and/or VL video acquired by the VL imaging system 104. The communication interface 150 includes a wireless electrical interface and/or an electro-mechanical physical connector.

The data repository 106 includes one or more of a picture archiving and communication system (PACS), a hospital information system (HIS), an electronic medical record (EMR), a server, a database, and/or other data repository. The data repository 106 stores information such as images generated by the VL imaging systems 102, . . . , 104 and/or other imaging systems. In the illustrated embodiment, a network 152 is in electronic communication with the communication interfaces 134 and 150 of the VL imaging systems 102, . . . , 104 and at least the image viewing station 108. The VL imaging systems 102, . . . , 104 and/or the at least the image viewing station 108 can push and/or pull data from the data repository 106.

Figure 2:
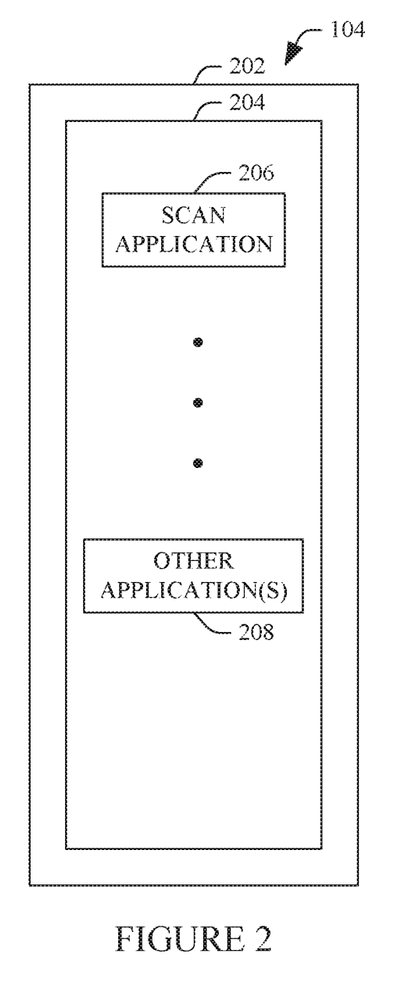
FIG. 2 schematically illustrates an example hand-held visible light imaging system visually displaying a touch sensitive scan application graphic.

FIG. 2 schematically illustrates an example of a sub-portion of the VL imaging system 104.

In this example, the VL imaging system 104 is a single enclosure, hand-held device such as a smartphone, a tablet, laptop, or the like. As such, the VL imaging system 104 includes a housing 202 and a touchscreen display 204. The housing 202 houses or encapsulates and/or supports electrical and mechanical components of the system 104 therein. The touchscreen display 204 is incorporated into and is part of a side of the housing 202. The touchscreen display 204, in this example, is an electronic visual display (e.g., a liquid crystal display, or LCD) with regions configured to be actuated by physical contact.

The touchscreen 204 allows an operator to run or invoke software instructions installed in the memory 144, e.g., the scan module 146. In the illustrated example, the controller 142 constructs and visually displays, when executing instructions of the scan module 146, one or more graphical soft controls or icons, each corresponding to a different software application stored in the memory 104. For example, in the illustrated example, the controller 104 displays a scan application graphic 206, . . . , other app(s) 208. Invoking the scan application graphic 206 causes the controller 142 to construct and visually display a plurality of graphical soft controls or icons, each corresponding to a different software application (or soft tool) of the scan application 206.

Figure 3:
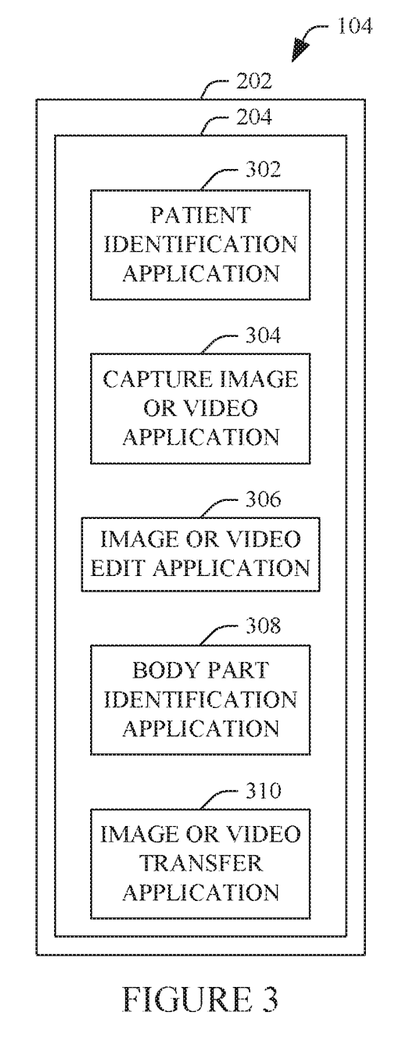
FIG. 3 schematically illustrates the example visible light imaging system visually displaying a plurality of touch sensitive scan application graphics of the scan application.
Figure 4:
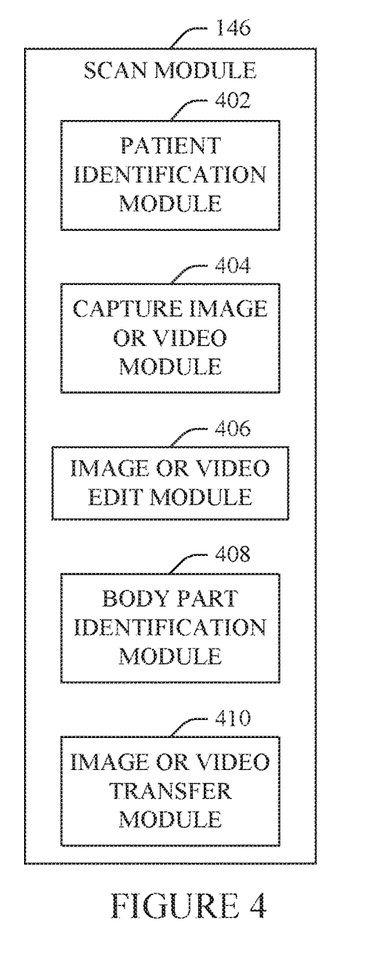
FIG. 4 schematically illustrates example software modules corresponding to the touch sensitive scan application graphics.

For example, as shown in FIG. 3, in the illustrated example, the controller 142 displays a patient identification graphic 302 for a patient identification application, a data capture graphic 304 for a capture image or video icon application, an edit graphic 306 for an image or video edit application, an annotate graphic 308 for an image or video body part identification application, and a data transfer graphic 310 for an image or video transfer application. FIG. 4 shows corresponding modules of the scan module 146, including a patient identification module 402, a capture image or video icon module 404, an image or video edit module 406, an image or video annotation module 408, and an image or video transfer module 410.

With reference to FIGS. 1-4, the patient identification application allows the operator to identify the patient that was/will be imaged with the VL imager 110. In one instance, the patient identification application allows an operator to select and/or provide a patient name. For example, in one instance, actuating the patient identification application graphic 302 presents a list of patient names, which are preloaded into the VL console 112, and the operator selects a patient name and/or identifier from the list with a mouse, a function key, etc. In another instance, actuating the patient identification application graphic 302 presents a search tool, which allows the operator to enter a patient name to search for the patient name in patient information pre-loaded onto the VL console 112.

In another instance, actuating the patient identification application 302 invokes, in response to an input from the UI 136, the acquisition circuitry 138 and image generator 140 to generate an image of quick response (QR) code. In this instance, the patient identification application extracts a unique medical record number (MRN) of the patient from the QR code. In another instance actuating the patient identification application 302 invokes, in response to an input from the UI 136, the acquisition circuitry 138 and image generator 140 to generate an image of a barcode. In this instance, the patient identification application extracts a unique MRN of the patient from the barcode. The QR code, the barcode, etc. can be stored on and scanned from a patient identification card, a patient file, a wrist band, an electronic medical record, etc.

Generally, MRNs are a method of identifying a patient and patient information by a number of organizations. For this, each provider organization of a set of organizations maintains a Master Patient Index (MPI) and the MRN is issued and maintained through this index. The MPI has included the patient's demographic information such as name, date of birth, address, mother's maiden name, SSN, etc. The MRN is used to identify an individual and his or her medical record/information. In general, it is designed to be unique only within a same organization. That is, the numbering system including the content and format of the MRN is usually specific to the individual organization.

Actuating the capture image or video application graphic 304 allows the operator to take capture a still visible light image and/or visible light video. For this, in one instance, the application visually presents pre-programmed scan protocols. Each scan protocol identifies at least one setting parameter, for example, a brightness, a resolution, a shutter speed, image or video mode, flash auto, on or off, etc. Other parameters are also contemplated herein. Alternatively, such parameters are included in a default configuration, user programmable configurations, etc. Alternatively, the operator manually sets one or more of the parameters. In one instance, protocol and/or configuration driven parameters are user adjustable.

Selection of a protocol and/or configuration by the operator causes the controller 142 to automatically load the at least one setting parameter. Alternatively, the at least one setting parameter is loaded in response to operator entry and/or change of a parameter. By way of non-limiting example, the operator selects a pre-programmed protocol for a skin rash. In this example, the at least one parameter disables or turns off the flash. Upon such selection, the controller 142 loads the flash off parameter. The operator, for example, can change this parameter to on or auto.

In one example, the capture image or video application also includes instructions which cause the controller 142 to guide the operator through on screen and/or audio instructions. For example, the instructions, in one example, guides an operator to take a predetermined number of visible light images and/or videos, in a particular order and in a particular way as specified in the imaging protocol. For example, the protocol may indicate that the operator should first take a longshot and then take a close up of the region of interest. The protocol may or may not allow the operator to take more than the predetermined number of pictures.

Actuating the capture image or video application graphic 304 visually presents soft controls for taking a visible light still image and/or visible light video using the acquisition circuitry 138 and the image generator 140 using the acquisition circuitry 138 and image generator 140. For visible light video, the controls include start record, pause, and stop. Such controls, for example, are through a same control, two controls, of three controls, including a single control for each of the functions record, pause, and stop. A scan of a patient may include visible light images only, visible light video only, or a combination of both visible light images and visible light video.

Actuating the image or video edit application graphic 306 allows the operator to edit a captured visible light still image and/or visible light video. For example, the image or video edit application allows the operator to perform one or more of the following functions: zoom, pan, crop, annotate with text and/or graphics, filter, convert a video frame to an image, shorten a video by removing frames, etc. The image or video edit application 306 also allows the operator to keep the original visible light image or visible light video, save the edited visible light image or visible light video, make a copy of a visible light image and/or visible light video, and/or other function related to the image and/or video.

Figure 5:
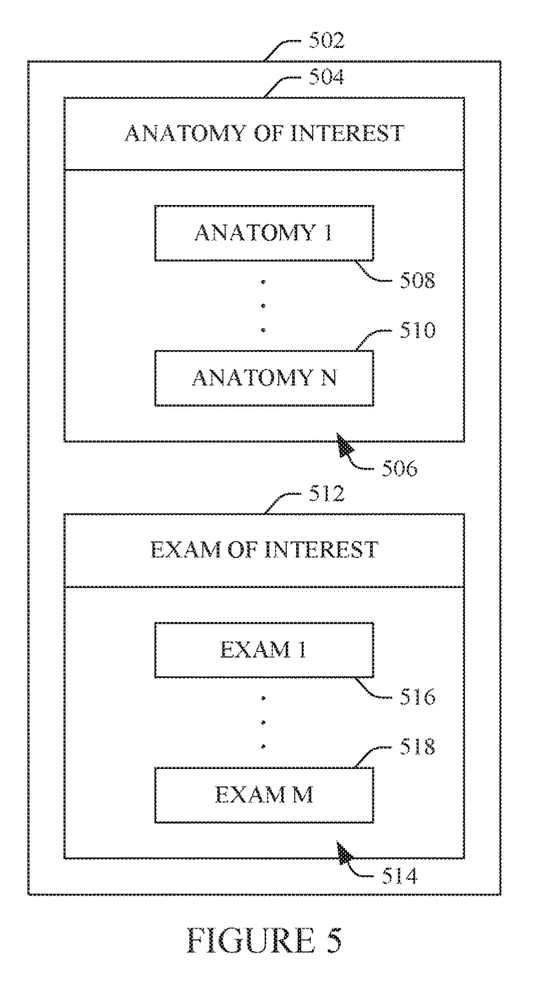
FIG. 5 schematically illustrates a soft menu for identifying an anatomy and examination of interest.

Actuating the body part identification application graphic 308 allows the operator to create a graphic that associates and/or identifies the body part captured in the visible light still image and/or visible light video. In one instance, invoking the body part identification application graphic 308 causes construction and display of a soft menu on the UI 136. An example soft menu 502 is shown in FIG. 5. The soft menu 502 includes a first sub-menu 504, which presents a first set of controls 506 corresponding to different anatomy 508, . . . , 510 (e.g., lower extremities, breast, abdomen, head, etc.) for anatomical regions of the body. The controls 506 are invokable via touch, mouse click, etc.

A second sub-menu 512 is also constructed and displayed on the UI 136. The second sub-menu 512 includes a second set of controls 514 of different exams 516, . . . , 518. The exams assigned to the controls 516, . . . , 518 correspond to an invoked one of the controls 508, . . . , 510; that is, the exams assigned to the controls 516, . . . , 518 are driven by the selected anatomy. Prior to invocation of a control 508 or 510, the controls 516, . . . , 518 may be inactive or assigned a default set of exams. Upon invocation of one of the controls 508, . . . , 510, the controls 516, . . . , 518 are assigned. For example, invoking a control 508 or 510 corresponding to the head causes head exams to be assigned to the controls 516, . . . , 518.

Figure 11:
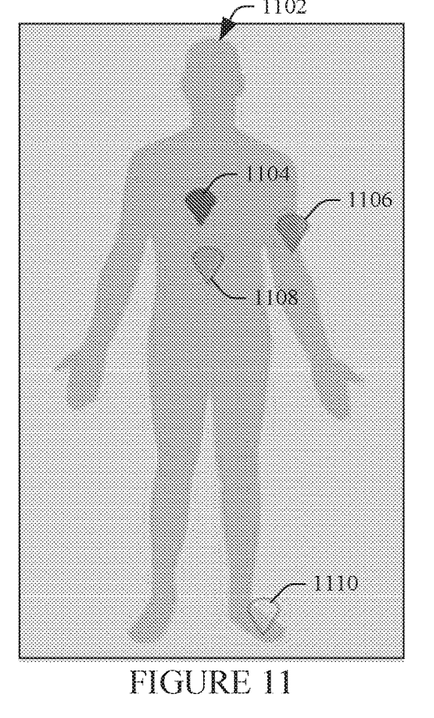
FIG. 11 schematically illustrates an example graphic representation of the human body.
Figure 12:
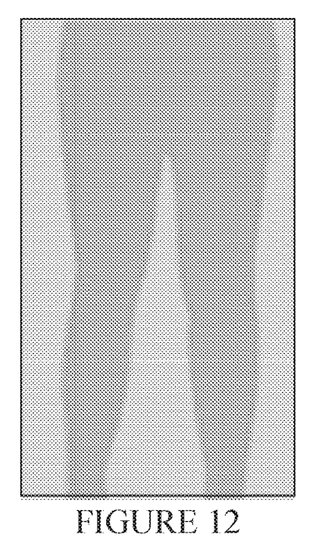
FIG. 12 schematically illustrates an example graphic representation of the lower extremities.
Figure 13:
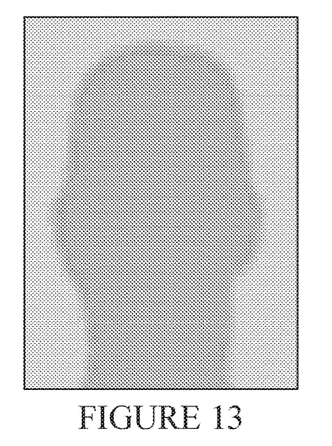
FIG. 13 schematically illustrates an example graphic representation of the head.
Figure 14:
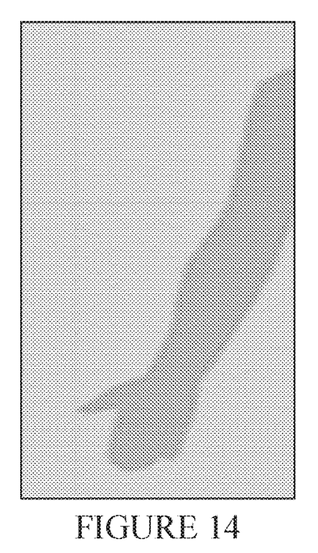
FIG. 14 schematically illustrates an example graphic representation of an upper extremity.

Invoking one of the exam controls 516, . . . , 518 causes construction and display of a graphic representation or model of a human or a sub-portion of a human. FIG. 11 shows an example representation of an entire human body graphical representation 1102. FIG. 12 shows an example representation of a lower extremity graphical representation 1202. FIG. 13 shows an example representation of a head graphical representation 1302. FIG. 12 shows an example representation of an upper extremity graphical representation 1402. Other graphical representations corresponding to other anatomy are also contemplated herein.

The graphical representations 1102, 1202, 1302 and 1402 are shown as two-dimensional profiles. However, it is to be understood that in a variation the graphics 1102, 1202, 1302 and 1402 are three-dimensional objects, actual images, etc. In either instance, the graphics 1102, 1202, 1302 and 1402 can be rotated, flipped (e.g., front/back and/or left/right), panned, zoomed, and/or otherwise manipulated. Furthermore, the graphics 1102, 1202, 1302 and 1402 include either a single layer (e.g., skin, as shown in FIGS. 11-14) or multiple layers such as skeletal, organ, skin, circulatory, etc. layers. The user can select the desired layer of interest through clicking on the graphic, controls, etc.

The graphics 1102, 1202, 1302 and 1402, in one example, is one from a set of graphics representing different gender, age, size, and/or other demographic. The body graphic 1102, in this example, is annotated with a plurality of graphic overlays. For example, in FIG. 11, the operator and/or device 104 has identified four locations 1104, 1106, 1108 and 1110 on the graphic 1102 which correspond to a region that was captured via a still VL image and/or VL video. In this example, the graphic is placed at each of the four locations 1104, 1106, 1108 and 1110.

The graphical representations 1102, 1202, 1302 and 1402 identify the four locations 1104, 1106, 1108 and 1110. In this example, the graphical representations 1102, 1202, 1302 and 1402 also provide other information. For example, a frequency of imaging in any area 1104, 1106, 1108 or 1110 is indicated by graphic intensity. In a variation, such information is conveyed through color, gray scale, size, etc. Where the patient being scanned has been previously scanned and images and/or video and/or an annotated graphic representation 1102, 1202, 1302 and 1402 is stored in the memory 144, areas of the body for which VL data for the specific patient already exists for the selected patient can be highlighted.

The graphic representation of the human, as a whole, provides an overview of the patient's history without having to sift through multiple records in PACS. Color and/or shape can be used to distinguish different episodes, which allows a clinical user to pick relevant studies for review and comparison. Hotspots are selectable and open the corresponding studies for viewing. When multiple entries map to a single spot, selecting the hotspot would open up a timeline that shows the different episodes for that body part. The body model or graphical representations 1102, 1202, 1302 and 1402 can also be used to categorize the visible light still images and/or visible light video based on date, body region, clinical question or reason, etc.

Actuating the image or video transfer application graphic 310 allows the operator to send VL still images and/or VL videos along with the annotated graphic representation 1102, 1202, 1302 and 1402 to the data repository 302. In one instance, the VL images and/or VL video are automatically removed from the VL imaging systems 102, . . . , 104 in response to completion of the transfer. In another instance, the VL images and/or VL video are manually removed from the VL imaging systems 102, . . . , 104, e.g., in response to the controller 120 and/or 142 receiving a removed command signal from the UI 114 and/or 136 indicative of an input of an operator to remove the VL images and/or VL video.

Figure 6:
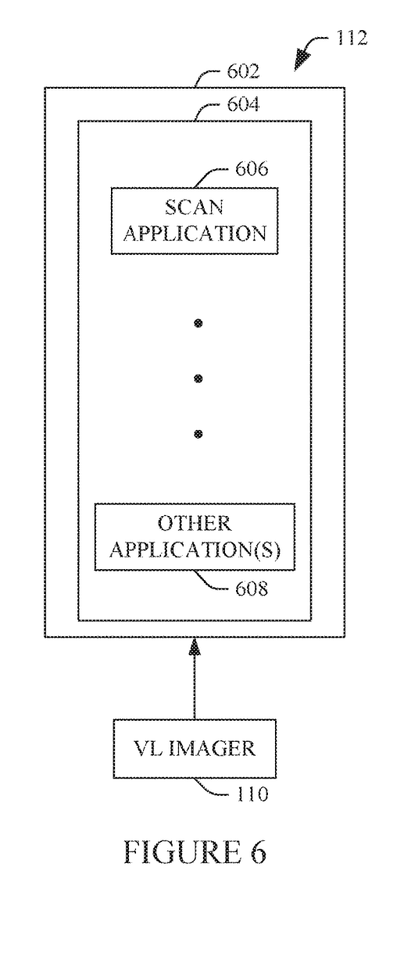
FIG. 6 schematically illustrates an example console of a visible light imaging system, which includes separate imager and console devices, visually displaying a touch sensitive scan application graphic.

FIG. 6 schematically illustrates an example of a portion of the VL imaging system 102, including the VL imager 110 and a display monitor 602 of the VL console 112. The VL imager 110, as discussed above, includes a device such as an endoscope, a microscope, a colposcope, a retinoscope, etc.

The display monitor 602 includes a display region 604. The display region 604 may include a touchscreen and/or non-touchscreen display. In either instance, display monitor 604 visually displays a scan application 606, . . . , other application(s) 608 of the scan module 128. Similar to the touchscreen 204 of FIG. 2, actuating the scan application 606, causes the processor 124 to visually display a plurality of graphical icons, each corresponding to a different software application of the scan application 606.

Figure 7:
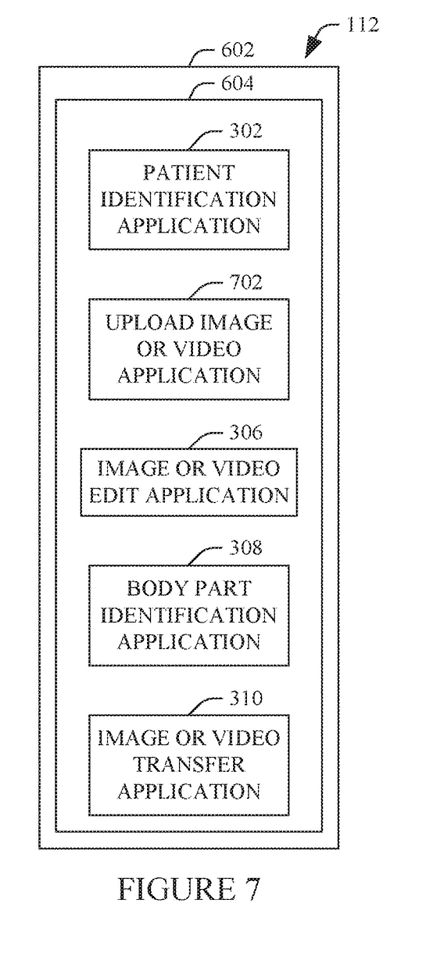
FIG. 7 schematically illustrates the example visible light imaging system visually displaying a plurality of touch sensitive scan application graphics of the scan application.
Figure 8:
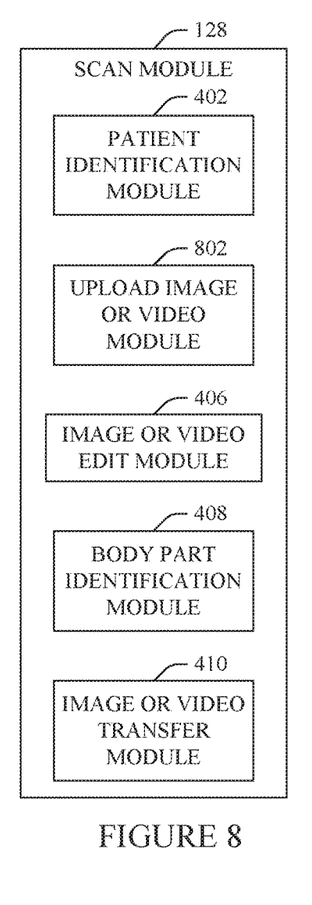
FIG. 8 schematically illustrates example software modules corresponding to the touch sensitive scan application graphics.

For example, as shown in FIG. 7, in the illustrated example, the processor 124 displays the patient identification application graphic 302, a data upload graphic 702 for an upload image or video icon application, the edit application graphic 306, the annotate application graphic 308, and the data transfer application graphic 310. FIG. 8 shows the corresponding modules of the scan module 128, including the patient identification module 402, an upload image or video icon module 802, the image or video edit module 406, the image or video annotation module 408, and the image or video transfer module 410.

With reference to FIGS. 1 and 6-8, actuating the patient identification application graphic 302 allows the operator to identify the patient that was imaged with the VL imager 110, as discussed in connection with FIGS. 1-4. For identifying such information using a QR code, a barcode, etc., the VL console 112 includes a scanner. Actuating the upload image or video application graphic 702 allows the operator to upload a still image and/or video from the VL imager 110 through the communication interfaces 122 and 134.

Actuating the image or video edit application graphic 306 allows the operator to edit a captured still image and/or video, as discussed in connection with FIG. 3 and/or otherwise. Actuating the body part identification application graphic 308 allows the operator to create a graphic that identifies the body part capture in the image and/or video, as discussed in connection with FIG. 3 and/or otherwise. Actuating the image or video transfer application graphic 310 allows the operator to send images and/or videos along with the graphic representation of the human to the data repository 302, as discussed in connection with FIG. 3 and/or otherwise.

Figure 9:
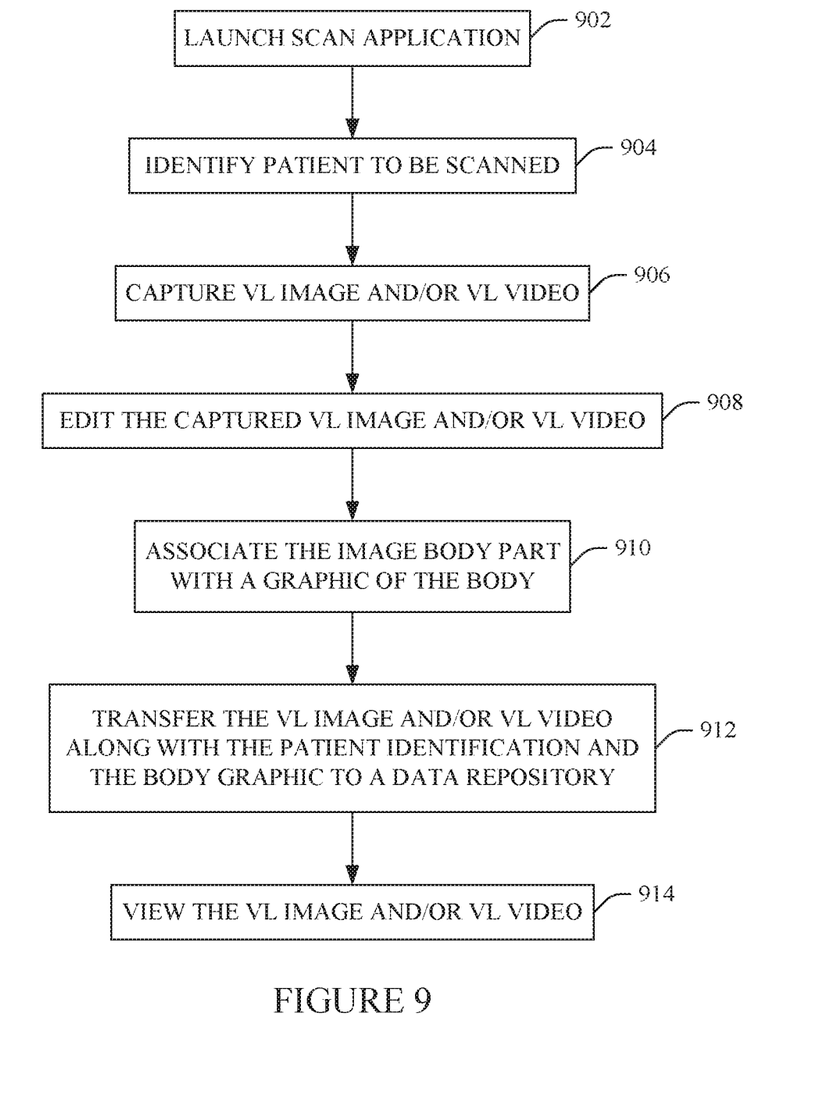
FIG. 9 illustrates an example method in accordance with a hand-held VL imaging system.

FIG. 9 illustrates an example flow chart in connection with the VL imaging system 104.

It is to be appreciated that the ordering of the acts in the methods described herein is not limiting. As such, other orderings are contemplated herein. In addition, one or more acts may be omitted and/or one or more additional acts may be included.

At 902, the scan application graphic 606 is actuated via the UI 136, executing the scan module 146.

At 904, the patient identification application graphic 302 is actuated to select a patient identification corresponding to the patient being imaged, as described herein and/or otherwise.

At 906, the capture image or video application graphic 304 is actuated to capture at least one of a VL image and/or a VL video of the patient, as described herein and/or otherwise.

At 908, the image or video edit application graphic 306 is actuated to edit the captured at least one of the VL image and/or the VL video, as described herein and/or otherwise.

At 910, the body part identification application graphic 308 is actuated to identify the scanned body part, as described herein and/or otherwise.

At 912, the at least one of the VL image and/or the VL video along with the patient identification and the annotated representation of the human are transferred to the data repository 106, as described herein and/or otherwise.

At 914, the at least one of the VL image and/or the VL video of the patient can be viewed through the image viewing station 108.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

Figure 10:
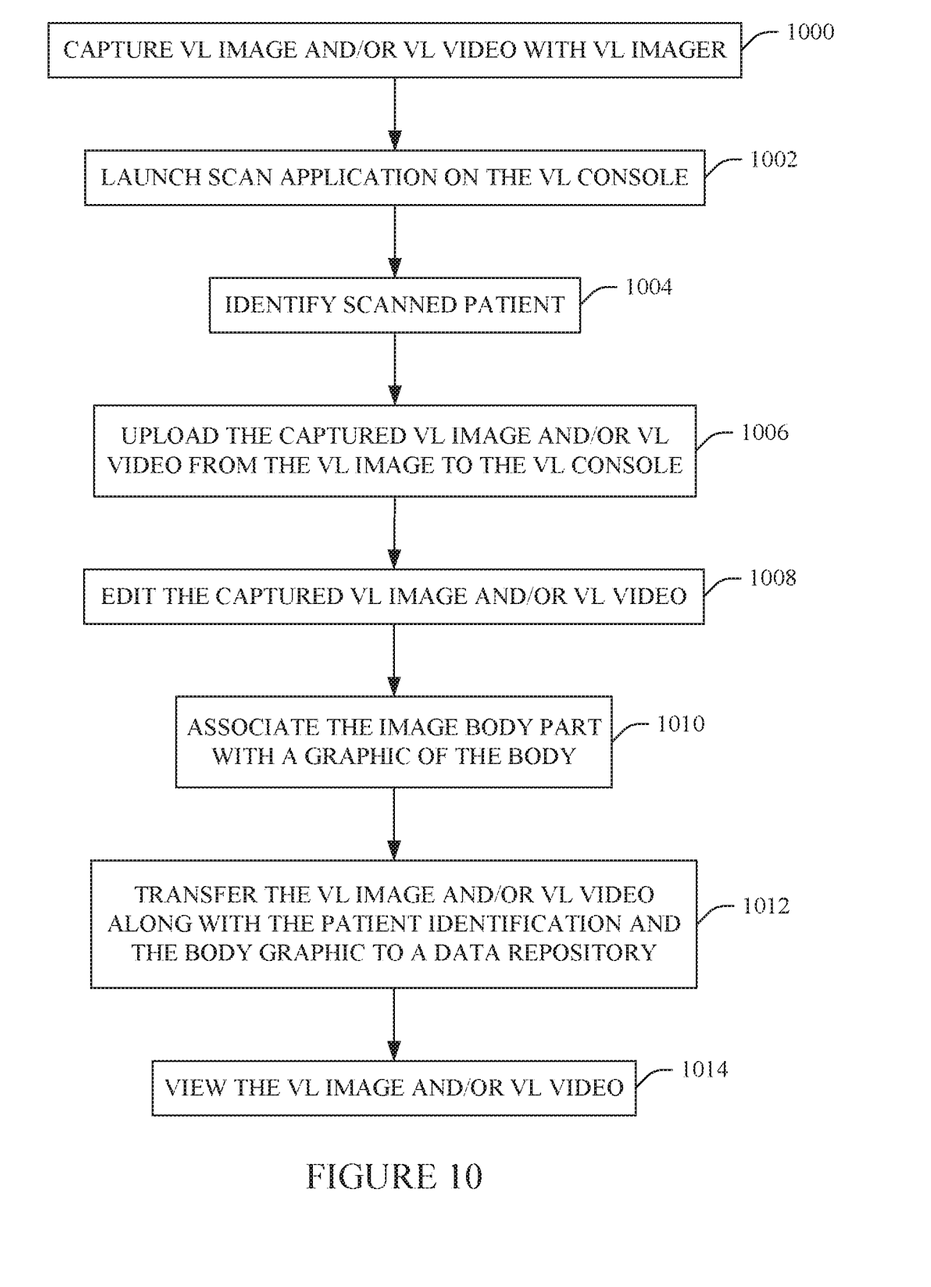
FIG. 10 illustrates an example method in accordance with a VL imaging system including separate imager and console devices.

FIG. 10 illustrates an example flow chart in connection with the VL imaging system 102.

It is to be appreciated that the ordering of the acts in the methods described herein is not limiting. As such, other orderings are contemplated herein. In addition, one or more acts may be omitted and/or one or more additional acts may be included.

At 1000, at least one of a VL image or a VL video is captured with the VL imager 110, as described herein and/or otherwise.

At 1002, the scan application graphic 206 is actuated via the UI 132 on the VL console 112, launching the scan module 146.

At 1004, the patient identification application graphic 302 is actuated to select a patient identification corresponding to the imaged patient, as described herein and/or otherwise.

At 1006, the upload image or video application graphic 702 is actuated to upload the captured at least one of the VL image and/or the VL video from the VL imager 110 to the VL console 112, as described herein and/or otherwise. The uploaded at least one of the VL image and/or the VL video can be removed from the visible light imager 110.

At 1008, the image or video edit application graphic 306 is actuated to edit the captured at least one of the VL image and/or the VL video, as described herein and/or otherwise.

At 1010, the body part identification application graphic 308 is actuated to identify the scanned body part, as described herein and/or otherwise.

At 1012, the at least one of the VL image and/or the VL video along with the patient identification and the annotated representation of the human are transferred to the data repository 106, as described herein and/or otherwise.

At 1014, the at least one of the VL image and/or the VL video of the patient can be viewed through the image viewing station 108.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The example(s) discussed herein allow for secure patient image and/or video capture. For example, images and/or video, once captured do not have to remain on the VL imaging systems 102 and 104 as they are pushed to long-term storage such as the data repository 106 and can be deleted from the VL imaging systems 102 and 104. Furthermore, the images and/or video are associated with the corresponding patient and/or patient's electronic patient records and imaged body part via the body model. Optionally, the manufacturer, model, device information, etc. of the VL imaging systems 102 and 104 can also be associated and stored along with the images and/or video.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A visible light imaging system, comprising:
    acquisition circuitry configured to sense visible light and generate a signal indicative thereof in connection with scanning a sub-portion of tissue of a subject;
    an image generator configured to generate at least one of a visible light image and a visible light video with the signal;
    a memory configured to store a scan module, which includes computer executable instructions; and
    a controller, which, in response to executing the computer executable instructions, performs the following acts:
        visually presents, in response to a first input signal, a first soft tool that retrieves an identification of a subject of interest to an imaging study based on a user input;
        associates the retrieved identification of the subject and the at least one of the visible light image and the visible light video of the subject;
        constructs a soft menu with a first sub-menu with first controls for selecting anatomy corresponding to the scanned tissue;
        constructs the soft menu with a second sub-menu with second controls for selecting a type of examination performed for the selected anatomy,
        constructs a graphical representation of at least a sub-portion of a subject based on the selected anatomy and the selected type of examination;
        receives an input indicating a location of the scanned tissue on the constructed graphical representation;
        superimposes an overlay over the indicated location on the graphical representation; and
        transfers the at least one of the visible light image and the visible light video with the associated identification of the subject and the superimposed overlay to a data repository.

2. The visible light imaging system of claim 1, wherein the controller, in response to executing the computer executable instructions, further:
  constructs the graphical representation of at least the sub-portion of the subject based on one or more of a gender of the subject, an age of the subject, or a desired orientation of the subject.

3. The visible light imaging system of claim 2, wherein the graphical representation includes at least two overlays, including an overlay superimposed over the graphical representation at an earlier date in response to a different imaging event, and at least one of a different intensity, color, gray scale, or size is used for the at least two overlays.

4. The visible light imaging system of claim 3, wherein the at least two overlays are located at a same location, and the controller, in response to clicking on one of the at least two overlays, visually presents a timeline that shows the corresponding two imaging events for the same location.

5. The visible light imaging system of claim 1, wherein the controller, in response to executing the computer executable instructions, further:
  visually presents, in response to a second input signal, an image and/or video editing soft tool;
  receives an edit command, which indicates an edit function to the at least one of the visible light image and the visible light video; and
  performs the edit function, thereby creating at least one of an edited visible light image and an edited visible light video.

6. The visible light imaging system of claim 5, wherein the edit function includes one or more of: a zoom, a pan, a crop, a rotate, a flip, an annotate with text, an annotate with a graphic, a filter, a convert a video frame to an image, a change gender, or a shorten a video by removing a frame function.

7. The visible light imaging system of claim 1, further comprising:
  a visible light imager that includes the acquisition circuitry, the image generator, and a console communication interface; and
  a visible light console that includes the memory, the controller, and an imager communication interface,
  wherein the visible light imager and the visible light console are separate apparatuses configured to communicate with each other through the console communication interface and the imager communication interface.

8. The visible light imaging system of claim 7, wherein the visible light imager includes at least one of a pair of smartglasses with a visible light recorder, an endoscope, a microscope, a colposcope, a retinoscope, a digital camera, and a digital video recorder.

9. The visible light imaging system of claim 1, wherein the visible light imaging system is a single enclosure, hand-held apparatus, and further comprising:
  a single housing that houses all of the acquisition circuitry, the image generator, the memory, and the controller; and
  a user interface integrated with and part of the housing.

10. The visible light imaging system of claim 9, wherein the visible light imaging system includes one of a smartphone, a tablet, or a laptop.

11. The visible light imaging system of claim 1, wherein the controller, in response to executing the computer executable instructions, further:
  removes the at least one of the visible light image and the visible light video from the visible light imaging system in response to completion of the transfer.

12. The visible light imaging system of claim 11, wherein the controller automatically removes the at least one of the visible light image and the visible light video in response to completion of the transfer.

13. The visible light imaging system of claim 11, wherein the controller removes the at least one of the visible light image and the visible light video in response to receiving a remove command signal indicative of an input of an operator to remove the at least one of the visible light image and the visible light video.

14. The visible light imaging system of claim 1, wherein the controller in response to executing the computer executable instructions, annotates the graphical representation of the subject with a graphic located at a body part corresponding to the scanned tissue, and transfers the at least one of the visible light image and the visible light video along with the subject identification and the annotated graphical representation to the data repository.

15. The visible light imaging system of claim 1, wherein the controller, in response to executing the computer executable instructions, loads a set of imaging parameters based on one of a selected imaging protocol, a default configuration, a user defined configuration, and a manual entry of parameters.

* * * * *